United States Patent
Solomon et al.

(10) Patent No.: US 8,034,920 B2
(45) Date of Patent: Oct. 11, 2011

(54) NUCLEIC ACID PRIMERS AND PROBES FOR DETECTING BREAST CELLS

(75) Inventors: Natalie A. Solomon, Buffalo Grove, IL (US); Lisa A Roberts-Rapp, Gurnee, IL (US)

(73) Assignee: Abbott Laboratories, Des Plaines, IL (US)

( * ) Notice: Subject to any disclaimer, the term of this patent is extended or adjusted under 35 U.S.C. 154(b) by 294 days.

(21) Appl. No.: 11/262,371

(22) Filed: Oct. 27, 2005

(65) Prior Publication Data

US 2006/0121504 A1  Jun. 8, 2006

Related U.S. Application Data

(63) Continuation-in-part of application No. 11/115,678, filed on Apr. 27, 2005, now abandoned, which is a continuation of application No. 08/962,094, filed on Oct. 31, 1997, now abandoned.

(60) Provisional application No. 60/622,822, filed on Oct. 28, 2004.

(51) Int. Cl.
C07H 21/04 (2006.01)
C12Q 1/68 (2006.01)

(52) U.S. Cl. .............. 536/24.33; 536/24.3; 536/24.31; 435/6.1; 435/91.2; 435/91.1

(58) Field of Classification Search .............. None
See application file for complete search history.

(56) References Cited

U.S. PATENT DOCUMENTS

| | | | |
|---|---|---|---|
| 2002/0177568 A1 * | 11/2002 | Stinchcomb et al. | 514/44 |
| 2003/0044859 A1 * | 3/2003 | Henslee et al. | 435/7.23 |
| 2003/0104410 A1 * | 6/2003 | Mittmann | 435/6 |
| 2003/0165971 A1 * | 9/2003 | Billing-Medel et al. | 435/6 |
| 2004/0265932 A1 * | 12/2004 | Henslee et al. | 435/7.23 |
| 2005/0153373 A1 * | 7/2005 | Billing-Medel et al. | 435/7.23 |
| 2005/0202499 A1 * | 9/2005 | Billing-Medel et al. | 435/6 |
| 2005/0214848 A1 * | 9/2005 | Billing-Medel et al. | 435/6 |

FOREIGN PATENT DOCUMENTS

| | | | |
|---|---|---|---|
| WO | WO 98/18945 | * | 5/1887 |
| WO | WO 97/44355 | * | 11/1997 |
| WO | WO 98/18945 A1 | | 5/1998 |
| WO | WO 01/65262 | * | 9/2001 |
| WO | WO 01/65262 A2 | | 9/2001 |
| WO | WO 01/75171 A2 | | 10/2001 |
| WO | WO 03/004989 A2 | | 1/2003 |
| WO | WO 2004/044123 A2 | | 5/2004 |
| WO | WO 2004/063355 A2 | | 7/2004 |

OTHER PUBLICATIONS

Colpitts et al. (Tumor Biology, vol. 23, pp. 263-278, 2002).*
Buck et al (Biotechniques (1999) 27(3):528-536).*
NEB catalog (1998/1999), pp. 121, 284.*
Oligo Primer analysis software, primer design. www.oligo.net, Aug. 20, 2008.*
Data Base Registry XP002371634, Sep. 3, 2004, retrieved from STN Database accession No. 738044-01-4.
Data Base EMBL XP002371635 (CM1-BT0738-250400-200-c12 BT0738 Homo sapiens cDNA, mRNA sequence), Jun. 23, 2000, retrieved from eBI accession No. EM_PRO:BE092421.

* cited by examiner

*Primary Examiner* — Jeanine A Goldberg
(74) *Attorney, Agent, or Firm* — Lisa V. Mueller; Michael Best & Friedrich LLP

(57) ABSTRACT

Polynucleotides are provided which are useful as amplification primers and hybridization probes for detecting BS106 target sequence in a test sample. The primers and probes can be employed in amplification based methods for detecting the presence of BS106 sequences in a test sample. Additionally, the primers and probes can be used to perform homogeneous, real time reverse-transcriptase polymerase chain reaction to detect BS106 target sequence in a test sample.

6 Claims, No Drawings

SEQUENCE LISTING

```
<160> NUMBER OF SEQ ID NOS: 13

<210> SEQ ID NO 1
<211> LENGTH: 120
<212> TYPE: DNA
<213> ORGANISM: Homo sapiens

<400> SEQUENCE: 1
accatgaagt tcttagcagt cctggtactc ttgggagttt ccatctttct ggtctctgcc      60
cagaatccga caacagctgc tccagctgac acgtatccag ctactggtcc tgctgatgat    120
```

```
<210> SEQ ID NO 2
<211> LENGTH: 21
<212> TYPE: DNA
<213> ORGANISM: Homo sapiens

<400> SEQUENCE: 2
accatgaagt tcttagcagt c                                              21

<210> SEQ ID NO 3
<211> LENGTH: 21
<212> TYPE: DNA
<213> ORGANISM: Homo sapiens

<400> SEQUENCE: 3
atcatcagca ggaccagtag c                                              21

<210> SEQ ID NO 4
<211> LENGTH: 15
<212> TYPE: DNA
<213> ORGANISM: Homo sapiens

<400> SEQUENCE: 4
cccagaatcc gacaa                                                     15

<210> SEQ ID NO 5
<211> LENGTH: 27
<212> TYPE: DNA
<213> ORGANISM: Homo sapiens

<400> SEQUENCE: 5
gtgctgccca gaatccgaca acagcac                                        27

<210> SEQ ID NO 6
<211> LENGTH: 18
<212> TYPE: DNA
<213> ORGANISM: Homo sapiens

<400> SEQUENCE: 6
gcccagaatc cgacaaca                                                  18

<210> SEQ ID NO 7
<211> LENGTH: 32
<212> TYPE: DNA
<213> ORGANISM: Homo sapiens

<400> SEQUENCE: 7
cgcgtgtgct ccagctgaca cgtatccacg cg                                  32

<210> SEQ ID NO 8
<211> LENGTH: 21
<212> TYPE: DNA
<213> ORGANISM: Homo sapiens

<400> SEQUENCE: 8
tctaccactg ctcgtaaaga c                                              21

<210> SEQ ID NO 9
<211> LENGTH: 21
<212> TYPE: DNA
<213> ORGANISM: Homo sapiens

<400> SEQUENCE: 9
ctcagggaca cactctacca t                                              21
```

```
<210> SEQ ID NO 10
<211> LENGTH: 28
<212> TYPE: DNA
<213> ORGANISM: Homo sapiens

<400> SEQUENCE: 10
gcgtgcaaat gggttgggga tctcacgc                                          28

<210> SEQ ID NO 11
<211> LENGTH: 22
<212> TYPE: DNA
<213> ORGANISM: Homo sapiens

<400> SEQUENCE: 11
tgcttctacc actgctcgta aa                                                22

<210> SEQ ID NO 12
<211> LENGTH: 25
<212> TYPE: DNA
<213> ORGANISM: Homo sapiens

<400> SEQUENCE: 12
ccatctcagg gacacactct accat                                             25

<210> SEQ ID NO 13
<211> LENGTH: 553
<212> TYPE: DNA
<213> ORGANISM: Homo sapiens
<220> FEATURE:
<221> NAME/KEY: misc_feature
<222> LOCATION: (543)...(544)
<223> OTHER INFORMATION: r=a or g

<400> SEQUENCE: 13
gaattcggct cgagcggctc gagctcttag gctttgaagc attttgtct  gtgctccctg       60 atcttcatgt caccaccatg aagttcttag cagtcctggt actcttggga gtttccatct      120
ttctggtctc tgcccagaat ccgacaacag ctgctccagc tgacacgtat ccagctactg      180
gtcctgctga tgatgaagcc cctgatgctg aaaccactgc tgctgcaacc actgcgacca      240
ctgctgctcc taccactgca accaccgctg cttctaccac tgctcgtaaa gacattccag      300
ttttacccaa atgggttggg gatctcccga atggtagagt gtgtccctga gatggaatca      360
gcttgagtct tctgcaattg gtcacaacta ttcatgcttc ctgtgatttc atccaactac      420
ttaccttgcc tacgatatcc cctttatctc taatcagttt attttctttc aaataaaaaa      480
taactatgag caacaaaaaa aaaaaaaaa  aaaaaaaaa  aaaaaaaaa  aaaaaaaaa       540 aargggcggc cgc                                                         553
```

NUCLEIC ACID PRIMERS AND PROBES FOR DETECTING BREAST CELLS

This application claims priority to U.S. provisional application No. 60/622,822 filed Oct. 28, 2004.

This application is a continuation-in-part of U.S. patent application Ser. No. 11/115,678, filed Apr. 27, 2005, which is a continuation of U.S. patent application Ser. No. 08/962,094, filed Oct. 31, 1997, now abandoned.

FIELD OF THE INVENTION

The present invention relates to oligonucleotides for detecting breast cells in a test sample.

BACKGROUND OF THE INVENTION

Breast cancer is the most common form of cancer occurring in females in the United States. The incidence of breast cancers in the United States is projected to be 180,200 cases diagnosed and 43,900 breast cancer related deaths to occur during 1997 (American Cancer Society statistics). The incidence of breast cancers in the United States is projected to be 213,910 cases diagnosed and 40,921 breast cancer related deaths to occur during 2004 (American Cancer Society statistics). Worldwide, the incidence of breast cancer has increased from 700,000 in 1985 to about 1,050,000 in 2000. G. N. Hortobagyi et al., C A *Cancer J. Clin.* 45: 199-226 (1995), Parkin D M., *Lancet Oncol.* 2(10):596 (2001).

Procedures used for detecting, diagnosing, staging, monitoring, prognosticating, preventing, treating or determining predisposition to diseases or conditions of the breast, such as breast cancer, are of critical importance to the outcome of the patient. For example, patients diagnosed with early breast cancer have greater than a 90% five-year relative survival rate as compared to a survival rate of about 20% of patients diagnosed with distantly metastasized breast cancers (American Cancer Society statistics). Currently, the best initial indicators of early breast cancer are physical examination of the breast and mammography. J. R. Harries et al. In: *Cancer: Principles and Practice of Oncology, Fourth Edition*, pp. 1264-1332, Philadelphia, Pa.: J/B. Lippincott Co. (1993). Mammography may detect a breast tumor before it can be detected by physical examination, but it has limitations. For example, mammography's predictive value depends on the observer's skill and the quality of the mammogram. In addition, 80% to 93% of suspicious mammograms are false positives, and 10% to 15% of women with breast cancer have false negative mammograms. C. J. Wright et al., *Lancet* 346: 29-32 (1995). Thereupon, new diagnostic methods which are more sensitive and specific for detecting early breast cancer are clearly needed.

A major concern with any cancer, including breast cancer, is the spread of the disease from a localized area (such as the breast) to other parts of the body (known as metastasis). Metastasis is believed to have occurred when epithelial cells are detected in the hematopoietic system. This discovery is important since metastasis is diagnostic of certain stages of cancer, and decisions concerning the proper treatment of a cancer patient are largely dependent upon properly characterizing the stage of the disease. In particular, the treatment of patients having localized cancer can be vastly different from the treatment of patients in metastatic stages of cancer.

Early efforts to detect the spread of cancer by detecting epithelial cells in the hematopoietic system included immunocytological assay procedures. Unfortunately, these methods are largely inaccurate because antibodies used in these assays that are ostensibly specific for epithelial cells, demonstrate cross-reactivity for cells normally found in the hematopoietic system. Hence, "normal hematopoietic cells" are sometimes detected in the absence of metastatic cells and therefore, false positive results can be obtained according to these assay procedures. Additionally, immunocytological assays lack sensitivity and can produce false negative results when low levels of epithelial cells are actually present in the hematopoietic system. Accordingly, early stages of metastatic cancer can be misdiagnosed using immunocytological assays.

With the advent of nucleic acid amplification reactions such as the polymerase chain reaction (PCR), epithelial cells present in the hematopoietic system can be detected via the nucleic acid instead of the protein. Hence, problems associated with cross-reactive antibodies are avoided. Additionally, it is well known that nucleic acid amplification reactions are significantly more sensitive than more conventional antibody based assay methods. Amplification based assays for detecting epithelial cells in the blood stream have therefore provided significant advantages over immunocytological assay methods for detecting early stages of metastatic cancer.

PCR based assays employed to detect epithelial cells in the hematopoietic system have been reported in the literature. Many of these assays target a nucleic acid sequence encoding cytokeratin 19 (CK19), a protein found on the surface of epithelial cells. However, pseudogenes (comprising a nucleic acid sequence that closely mimics the gene for CK19) are present in the human genome. Thus, one challenge facing those developing amplification assays to detect a CK19 target sequence is to design assays that amplify and detect a sequence from the CK19 gene but not the closely related pseudogene.

In addition to CK19, two other markers have been discovered that may be used to detect metastatic breast cancer cells. These two markers are termed BU101 (also called lipophilin B) and BS106 (also called small breast epithelial mucin or "SBEM"). (Colpitts et al., *Ann. NY Acad. Sci.* 923:312-315 (2000); Colpitts et al., *Tumor Biol.* 23:263-278 (2002)). These markers were found to be specifically expressed in breast epithelium. Measurements of the expression of these two markers have been made and compared to CK19. CK19 has been found to be highly sensitive in detecting all breast cancers, while BU101 and BS106 were found to be slightly more restrictive. The reason for this is that CK19 is highly expressed by most epithelial cells making it a very sensitive marker, but it cannot be considered breast specific. Thereupon, BU101 and BS106 are considered to be more breast specific markers compared to CK19. Therefore, BU101 and BS106 may provide sufficient discrimination to detect and measure occult breast cancer.

The cDNA sequence of BS106 has been studied and characterized. (Colpitts et al., *Tumor Biol.* 23:263-278 (2002)). It has been demonstrated that BS106 is expressed in mammary, salivary and prostate glands, but not in other tissues. The cDNA encodes a 90-amino acid protein characterized as a small, mucin-like protein, based on amino acid composition, extensive O-linked glycosylation, and expression profile. BS106 mRNA has been detected in 90% of the breast tissues examined.

BS106 mRNA expression has been detected in more than 90% of invasive ductal carcinomas. It was found that BS106 mRNA is expressed in breast cancer cell lines but not in cell lines of non-breast origin. This indicates that BS106 expression is a common feature of breast cancer and can serve as a useful marker for breast nodal metastasis, both for detection of micrometastatic cells within lymph nodes as well as in differential diagnosis of the primary origin of unknown metastasis.

However, known BS106 marker detection methods are cumbersome and non-specific. Some methods use a two-step cDNA production and then PCR while some methods use gel detection (TaqMan® PCR).

Additionally, another problem with known BS106 marker detection methods is that the primers and probes employed in such methods are not very specific or sensitive. In fact, it is well known that amplification primer sequences that are used for such detection methods can be selected based upon computer comparisons of closely related sequences. Theoretically, sequences selected in this manner effectively should produce copies of the selected target sequence when employed according to nucleic acid amplification principles. Notwithstanding the theoretical efficacy of sequences selected in the above manner, it is often times true that such sequences do not produce acceptable amounts of amplification product. Unfortunately, this phenomenon is not well understood. Accordingly, while primers initially can be screened using computer programs, efficacy cannot be adequately determined until such primers are employed in practice. This was especially true in the design of primers and probes for use in the amplification of BS106 mRNA. The inventors of the present invention found the design of primers and probes for use in the amplification of BS106 mRNA to be difficult because BS106 mRNA contains rather small introns, repetitive sequence strings and AT regions. Many of the primer pairs and probes selected by a computer program (such as OLIGO™) could not be used because these selections did not span the introns and had a high false priming potential with other human genes.

Therefore, there is a need in the art for a detection method that is simple and specific for a BS106 marker. Additionally, in connection with said detection method, there is a need for primer and probe sequences that can be used in said method and are highly specific and sensitive for the BS106 marker.

SUMMARY OF THE INVENTION

The present invention provides polynucleotide sequences that can be used to specifically and sensitively amplify and detect a BS106 target sequence. More specifically, in one embodiment, the present invention relates to a primer having a sequence that has a length of 15 to 40 nucleotides and comprises a segment that is at least about 80% identical to SEQ ID NO: 2, and complements thereof.

In another embodiment, the present invention relates to a primer having a sequence that has a length of 15 to 40 nucleotides and comprises a segment that is at least about 80% identical to SEQ ID NO: 3, and complements thereof.

In another embodiment, the present invention relates to a probe having a sequence that has a length of 12 to 40 nucleotides and comprises a segment that is at least about 80% identical to SEQ ID NO: 4, and complements thereof.

In yet another embodiment, the present invention relates to a composition of matter that comprises at least two (2) primer sequences. The first primer can have a sequence that has a length of 15 to 40 nucleotides and comprises a segment that is at least about 80% identical to SEQ ID NO: 2 and complements thereof. The second primer can have a sequence that has a length of 15 to 40 nucleotides and comprises a segment that is at least 80% identical to SEQ ID NO: 3. Optionally, this composition of matter can also comprise at least one probe sequence that has a sequence that has a length of 12 to 40 nucleotides and comprises a segment that is at least about 80% identical to the sequence shown in SEQ ID NO: 4. Alternatively, the probe sequence can have the sequence shown in SEQ ID NO: 5. Preferably, the probe sequence comprises at least one detectable label that is capable of generating a measurable signal.

A BS106 target sequence can be detected in a test sample in a number of different ways, in yet another embodiment of the present invention. For example, the BS106 target sequence can be amplified by forming a reaction mixture comprising nucleic acid amplification reagents, a test sample containing a BS106 target sequence and a primer set. The first primer in the primer set can have a sequence that has a length of 15 to 40 nucleotides and comprises a segment that is at least about 80% identical to SEQ ID NO: 2. The second primer in the primer set can have a sequence that has a length of 15 to 40 nucleotides and comprises a segment that is at least 80% identical to SEQ ID NO: 3. Optionally, the reaction mixture can also contain at least one probe. Following amplification, the amplified target sequence can be detected. If the reaction mixture does not contain a probe, the amplified target sequence can be detected using a variety of techniques known in the art, such as, but not limited to, gel electrophoresis. If the reaction mixture contains a probe, then the probe is hybridized to the amplified target sequence to form a probe/amplification product hybrid which can be detected. The probe that can be used to detect the amplified target sequence can be a probe having a sequence that has a length of from 12 to 40 nucleotides and comprises a segment that is at least about 80% identical to SEQ ID NO: 4. Such a probe can be a capture probe, a PNA probe, a TaqMan™ probe, a molecular beacon probe, etc. An example of a molecular beacon probe that can be used has the sequence shown in SEQ ID NO: 5.

If desired, the primers or probes can be labeled with at least one detectable label that is capable of generating a measurable signal to capture and detect the amplified BS106 target sequence or product hybrid and indicate the presence of the target sequence in the test sample. Moreover, the product hybrid can be detected using microparticle capture techniques. Preferably, when a probe having the sequence shown in SEQ ID NO: 5 is used to detect a BS106 target sequence in a test sample, said probe is labeled with at least one fluorophore and at least one quencher.

By way of another example, the presence of a BS106 target sequence can be detected in a test sample by first extracting mRNA from said test sample. Once this mRNA is extracted from a test sample, a reaction mixture can be formed. This reaction mixture can comprise, in addition to the extracted mRNA, enzymes having reverse transcriptase activity, nucleic acid amplification reagents, a pair of primers and at least one probe. One of the primers in the pair can have a sequence that has a length of 15 to 40 nucleotides and comprises a segment that is at least about 80% identical to SEQ ID NO: 2. The other primer in the pair can have a sequence that has a length of 15 to 40 nucleotides and comprises a segment that is at least 80% identical to SEQ ID NO: 3. The probe can have a sequence that has a length of from 12 to 40 nucleotides and comprises a segment that is at least about 80% identical to SEQ ID NO: 4. Preferably, the first primer in the pair has the sequence shown in SEQ ID NO: 2, the second primer in the pair has the sequence shown in SEQ ID NO: 3 and the probe has a sequence shown in SEQ ID NO: 5. Once the reaction mixture is formed, cDNA is generated from the mRNA. Once the cDNA has been generated, the reaction mixture is subjected to amplification conditions necessary to (i) generate an amplification product; and (ii) hybridize the probe to the amplification product to form a hybrid. Once the reaction mixture has been subjected to the amplification conditions, the hybrid can be detected. The detection of the hybrid can be made by labeling the probe (SEQ ID NO: 5) with at least one fluorophore and at least one quencher which can be detected using routine techniques known in the art. The presence of the hybrid is an indication of the presence of a BS106 target sequence in the test sample.

In yet still a further embodiment, the present invention also relates to kits for amplifying a BS106 target sequence. Such kits can comprise a primer having a sequence that has a length of 15 to 40 nucleotides and comprises a segment that is at least about 80% identical to SEQ ID NO:2 and a primer having a sequence that has a length of 15 to 40 nucleotides and comprises a segment that is at least 80% identical to SEQ ID NO: 3 and amplification reagents. Optionally, said kits can contain a primer having the sequence shown in SEQ ID NO: 2 and a primer having the sequence shown in SEQ ID NO: 3. Optionally, said kits can further comprise a probe having a length of 12 to 40 nucleotides and comprises a segment that is at least about 80% identical to the sequence comprising SEQ ID NO: 4 or a probe having the sequence shown in SEQ ID NO:5.

DETAILED DESCRIPTION OF THE INVENTION

Definitions

As used herein, the term "amplification conditions" refers to conditions which promote the hybridizing or annealing of primer sequences to a target sequence and subsequent extension of the primer sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or $T_m$, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will be employed. Since ionic strength is typically optimized for enzymatic activity, the only parameter left to vary is the temperature. Generally, the hybridization temperature is selected close to or at the $T_m$ of the primers or probe. Thus, obtaining suitable hybridization conditions for a particular primer, probe, or primer and probe set can be determined by one skilled in the art.

As used herein, the term "BS106" refers to a protein expressed in breast epithelium that is also known as small breast epithelial mucin or "SBEM".

As used herein, the term "label" refers to a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

As used herein, the term "microparticle", refers to any material which is insoluble, or can be made insoluble by a subsequent reaction and is in a particulate form. Thus, microparticles can be latex, plastic, derivatized plastic, magnetic or non-magnetic metal, glass, silicon or the like. A vast array of microparticle configurations are also well known and include, but are not intended to be limited to, beads, shavings, grains, or other particles, well known to those skilled in the art. Microparticles according to the present invention preferably are between 0.1 µM and 1 µM in size and more preferably between 0.3 µM and 0.6 µM in size.

As used herein, the term "nucleic acid amplification reagents" refers to conventional reagents that are employed in amplification procedures (such as, but not limited to, polymerase chain reaction (PCR), reverse transcription PCR (RT PCR), etc.) which are well known and may include, but are not limited to, one or more enzymes that have polymerase activity or reverse transcriptase activity, enzyme cofactors (such as magnesium or manganese; salts; nicotinamide adenine dinucleotide (NAD)), salts, buffers and deoxynucleotide triphosphates (dNTPs, for example, deoxyadenine triphosphate, deoxyguanine triphosphate, deoxycytosine triphosphate and deoxythymine triphosphate) and other reagents that modulate the activity of the enzymes or the specificity or sensitivity of the primers or probes.

As used herein, the term "polynucleotide(s)" refers to a polymer of DNA or RNA, modified DNA or RNA, DNA or RNA mimetics or nucleic acid analogs such as uncharged nucleic acid analogs including, but not limited to, peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. As used herein, the term "polynucleotide", includes polynucleotides composed of naturally-occurring nucleobases, sugars and covalent internucleoside (backbone) linkages as well as polynucleotides having non-naturally-occurring portions which function similarly. Polynucleotides can routinely be synthesized using a variety of techniques that are currently available. For example, such sequences can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference. It will be understood, however, that the sequences employed as primers should at least comprise DNA at the 3' end of the sequence and preferably are completely comprised of DNA.

As used herein, the term "solid support", refers to any material which is insoluble, or can be made insoluble by a subsequent reaction. Thus, a solid support can be can be latex, plastic, derivatized plastic, magnetic or non-magnetic metal, glass, silicon or the like. A vast array of solid support configurations are also well known and include, but are not intended to be limited to, beads, shavings, grains, particles, plates, or tubes.

As used herein, the term "segment" refers to an oligonucleotide that can be a partial sequence of entire nucleic acid sequence of a polynucleotide. The present invention also contemplates that a "segment" can comprise an entire nucleic acid sequence of a polynucleotide.

As used herein, the term "specifically hybridizes" refers to the ability of a nucleic acid to bind detectably and specifically to a second nucleic acid. Polynucleotides specifically hybridize to target nucleic acid strands under hybridization and wash conditions that minimize appreciable amounts of detectable binding to non-specific nucleic acids. High stringency conditions can be used to achieve specific hybridization conditions as known in the art. The skilled artisan will appreciate that some degree of mismatch or sequence overhang can be tolerated without departing from the spirit and scope of the present invention.

As used herein, the term "target sequence" refers to a polynucleotide sequence that is detected, amplified, both amplified and detected or otherwise is complementary to one of the polynucleotide sequences herein provided. While the term target sequence is sometimes referred to as single stranded, those skilled in the art will recognize that the target sequence may actually be double stranded.

As used herein, the term "test sample" refers to anything suspected of containing the target sequence. The test sample can be derived from any biological source, such as for example, blood, bone marrow, bronchial alveolar lavage, saliva, throat swabs, ocular lens fluid, cerebral spinal fluid, sweat, sputa, urine, milk, ascites fluid, mucous, synovial fluid, peritoneal fluid, anionic fluid, tissues such as lymph nodes or heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like. Most typically, the test sample will be peripheral blood, lymph nodes or bone marrow.

THE PRESENT INVENTION

The present invention provides primers, probes, compositions of matter, reagents, methods, and kits for amplifying and detecting a BS106 target sequence in a test sample.

Primers and Probes

The present invention relates to certain polynucleotide sequences (shown in SEQ ID NOS: 2, 3, 4 and 5) that can be used as primers and probes. In particular, the present invention provides at least two polynucleotide sequences that can be employed, either individually or together, as amplification primers to amplify a BS106 target sequence. The BS106 target sequence can be a RNA, DNA or cDNA sequence. Preferably, the BS106 target sequence is a RNA sequence. The cDNA sequence that encodes BS106 is provided for in WO 98/18945, which is herein incorporated by reference, and shown in SEQ ID NO: 13. SEQ ID NO: 1 is a portion of the cDNA sequence shown in SEQ ID NO: 13.

More specifically, one of the primer sequences of the present invention is a polynucleotide that specifically hybridizes to a BS106 target sequence, has a length of 15 to 40 nucleotides (i.e., a length of 15, 16, 17, 18, 19, 20, 21, 22, 23, 24, 25, 26, 27, 28, 29, 30, 31, 32, 33, 34, 35, 36, 37, 38, 39 or 40 nucleotides) and comprises a segment that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the sequence set forth in SEQ ID NO: 2. The second primer sequence of the present invention is a polynucleotide that specifically hybridizes to a BS106 target sequence, has a length of 15 to 40 nucleotides (i.e., a length of 15, 16, 17, 18, 19, 20, 21, 22, 23, 24, 25, 26, 27, 28, 29, 30, 31, 32, 33, 34, 35, 36, 37, 38, 39 or 40 nucleotides) and comprises a segment that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the sequence set forth in SEQ ID NO: 3. Complements of both of the above described primer sequences are also contemplated and within the scope of the present invention. The percent identity between two nucleic acid sequences can be determined by a number of methods well-known in the art, for example, by using the BLASTN program of the University of Wisconsin Computer Group (GCG) software.

For the purposes of the present invention, primer sequences that specifically hybridize to a BS106 target sequence, have a length of 15 to 40 nucleotides and comprise a segment that is at least about 80% identical to the sequence set forth in SEQ ID NO: 2 or SEQ ID NO: 3 as described above are considered to be homologues of the primer sequences of the present invention. The term "homologue(s)" as used herein, includes polynucleotides comprising SEQ ID NO: 2 or SEQ ID NO: 3 in which there are additions, deletions, and minor substitutions. For example, a primer comprising the nucleic acid sequence set forth in SEQ ID NO: 2 or SEQ ID NO: 3 in which nucleotides have been deleted from either the 3' or 5' end, or from both ends, and which retain the ability to specifically hybridize to a BS106 target sequence are considered to be homologues and within the scope of the present invention.

In the present invention, primer sequences that specifically hybridize to a BS106 target sequence, have a length of 15 to 40 nucleotides and comprises a segment that is at least 80% identical to the sequence set forth in SEQ ID NO: 2 can be used as a forward primer. Primer sequences that specifically hybridize to a BS106 target sequence, have a length of 15 to 40 nucleotides and comprise a segment that is at least 80% identical to the sequence set forth in SEQ ID NO: 3 can be used as a reverse primer. A primer sequence having a sequence set forth in SEQ ID NO: 3 is particularly useful as this primer spans an intron in the BS106 gene and thus provides a mechanism for differentiating between mRNA and genomic DNA (BS106) target sequences.

In addition to the primers described herein, the present invention also provides at least one probe sequence that can be used to detect a BS106 target sequence in a test sample. Preferably the at least one probe sequence is used with the hereinbefore described primers to detect a BS106 target sequence in a test sample. The probe sequence that can be used is a polynucleotide that specifically hybridizes to a BS106 target sequence, has a length of 12 to 40 nucleotides (i.e., a length of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides) and comprises a segment that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the sequence set forth in SEQ ID NO: 4. Complements of the above described probe sequence are also contemplated and within the scope of the present invention. As discussed earlier, the percent identity between two nucleic acid sequences can be determined by a number of methods well-known in the art, for example, by using the BLASTN program of the University of Wisconsin Computer Group (GCG) software.

For the purposes of the present invention, probe sequences that specifically hybridize to a BS106 target sequence, have a length of 12 to 40 nucleotides and comprise a segment that is at least about 80% identical to the sequence set forth in SEQ ID NO:4 as described above are considered to be homologues of the probe sequences of the present invention. The term "homologue(s)" as used herein, includes polynucleotides comprising SEQ ID NO: 4 in which there are additions, deletions, and minor substitutions. For example, a probe comprising the nucleic acid sequence set forth in SEQ ID NO: 4 in which nucleotides have been deleted from either the 3' or 5' end, or from both ends, and which retain the ability to specifically hybridize to a BS106 target sequence are considered to be homologues and within the scope of the present invention.

The probes of the present invention can be used as capture probes, PNA probes, TaqMan® probes, molecular beacon probes, etc.

TaqMan® probes are dual-labeled fluorogenic probes composed of a polynucleotide complementary to the target sequence that is labeled at the 5' terminus with a fluorophore and with a quencher at either the 3' terminus or at some other base up to a few nucleotides away from the fluorophore. TaqMan® probes are typically used as real-time probes in amplification reactions. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and produce a detectable signal. Methods for making TaqMan® probes are described in U.S. Pat. Nos. 5,210,015 and 5,487,972.

Molecular beacon probes are well-known in the art and are described U.S. Pat. Nos. 6,150,097, 5,925,517 and 6,103,476. Basically, molecular beacons are polynucleotide probes capable of forming a stem-loop (hairpin) structure. The loop is a single-stranded structure containing sequences complementary to the target sequence, whereas the stem typically is unrelated to the target sequence and self-hybridizes to form a double-stranded region. Nucleotides that are both complementary to the target sequence and that can self-hybridize may also form part of the stem region. Attached to one arm of the stem is a fluorophore moiety and to the other arm a quencher moiety. When the polynucleotide adopts a hairpin shape, the fluorophore and the quencher are in close proximity and the energy emitted by the fluorophore is thus absorbed by the quencher and given off as heat, resulting in internal quenching of the fluorophore. Upon binding of the polynucleotide to its target sequence, the fluorophore and the quencher become spatially separated and the fluorophore can fluoresce producing a detectable signal.

The present invention further contemplates the use of the BS106 specific, genotype-independent polynucleotides as linear probes in conjunction with a fluorophore and a high efficiency dark quencher, such as the Black Hole Quenchers (BHQ™; Biosearch Technologies, Inc., Novato, Calif.). As is known in the art, the high quenching efficiency and lack of native fluorescence of the BHQ™ dyes allows "random-coil" quenching to occur in linear probes labeled at one terminus with a fluorophore and at the other with a BHQ™ dye thus ensuring that the fluorophore does not fluoresce when the probe is in solution. Upon binding its target sequence, the probe stretches out, the fluorophore and quencher are thus spatially separated and the fluorophore fluoresces. One skilled in the art will appreciate that the BHQ™ dyes can also be used as the quencher moiety in molecular beacon or TaqMan® probes.

Suitable fluorophores and quenchers for use with the polynucleotides of the present invention can be readily determined by one skilled in the art (see also, Tgayi et al., *Nature Biotechnol.* 16:49-53 (1998); Marras et al., *Genet. Anal.: Biomolec. Eng.* 14:151-156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives such as FAM, VIC, and JOE, 5-(2'-aminoethyl)aminonaphthalene-1-sulphonic acid (EDANS), coumarin and coumarin derivatives, Lucifer yellow, NED, Texas red, tetramethylrhodamine, tetrachloro-6-carboxyfluoroscein, 5 carboxyrhodamine, cyanine dyes and the like. Quenchers include, but are not limited to, DABSYL, 4'-(4-dimethylaminophenylazo)benzoic acid (DABCYL), 4-dimethylaminophenylazophenyl-4'-maleimide (DABMI), tetramethylrhodamine, carboxytetramethylrhodamine (TAMRA), BHQ™ dyes and the like. Methods of coupling fluorophores and quenchers to nucleic acids are well-known in the art.

Preferably, the probes of the present invention are molecular beacon probes. As is known in the art, certain criteria need to be met for a molecular beacon probe to be successful in monitoring or detecting an amplification reaction. The present invention, therefore, provides a molecular beacon probe that comprises the polynucleotide of the present invention together with self-complementary regions. The polynucleotide of the present invention, may make up the loop region of the molecular beacon, or may make up the loop region and part of the stem region. Thus, the self-complementary stem sequences can be unrelated to the target sequence or may contain one or more nucleotides which are complementary to the target sequence.

As is known in the art, molecular beacon probes can be used to monitor the progress of an amplification reaction in real time. During the course of an amplification reaction, such as PCR, the molecular beacon interacts with its target sequence at the anneal temperature for the probe and a fluorescent signal is generated. As the number of target strands produced in the amplification reaction increases, the number of molecular beacons bound to their target increases concomitantly, as does the strength of the fluorescent signal.

Most preferably, the molecular beacon probe to be used in the present has the sequence shown in SEQ ID NO: 5 (5'-GTGCTG CCCAGA ATCCGAC AACAGCAC-3'). The bolded sequences shown above in SEQ ID NO: 5 are non-BS106 cDNA consensus sequences that have been added to help form the stem of the molecular beacon. The underlined sequences form the entire molecular stem of the beacon. One of the important aspects of this probe is that it spans an intron in the BS106 gene which eliminates or minimizes the detection of genomic DNA. For use in detecting a BS106 target sequence, SEQ ID NO: 5 can be labeled with a suitable fluorophore and quencher using routine techniques known to the ordinary artisan.

Methods for Amplifying and Detecting BS106 Target Sequences in a Test Sample

In one embodiment, at least two primers are used as amplification primers according to amplification procedures known in the art to amplify a BS106 target sequence in a test sample. Specifically, one of the primers has a length of 15 to 40 nucleotides and comprises a segment that is at least about 80% identical to SEQ ID NO: 2 and a second primer has a length of 15 to 40 nucleotides and comprises a segment that is at least 80% identical to SEQ ID NO: 3. The primer sequences described herein can be employed in a variety of amplification procedures known in the art such as, but not limited to, PCR (which is described in U.S. Pat. Nos. 4,683,195 and 4,683,202), nucleic acid sequence based amplification (NASBA), strand displacement amplification (SDA), etc. It will be understood by those skilled in the art that since the BS106 target sequence is RNA, a reverse transcription step should be included in the amplification of the BS106 target sequence. Enzymes having reverse transcriptase activity, such as rTth, are well known for activity capable of synthesizing a DNA sequence from an RNA template. Reverse transcription PCR (RT PCR) is well known in the art and described in U.S. Pat. Nos. 5,310,652 and 5,322,770 which are herein incorporated by reference, and is also contemplated as a suitable amplification procedure for use in the present invention. Additionally, one skilled in the art will recognize that for use in certain amplification procedures that the primers of the present invention may need to be modified, for example, for SDA, the primers will comprise additional nucleotides near their 5' end that constitute a recognition site for a restriction endonuclease. Similarly, for NASBA, the primer comprises additional nucleotides near the 5' end that constitute a RNA polymerase promoter. Polynucleotides modified in this manner are considered within the scope of the present invention.

Thus, amplification methods of the present invention generally comprise the steps of (a) forming a reaction mixture comprising nucleic acid amplification reagents, at least two primers, wherein one of the primers has a length of 15 to 40 nucleotides and comprises a segment that is at least about 80% identical to SEQ ID NO: 2 and the second primer has a length of 15 to 40 nucleotides and comprises a segment that is at least 80% identical to SEQ ID NO: 3 and a test sample suspected of containing a BS106 target sequence; and (b) subjecting the mixture to amplification conditions to generate at least one copy of the BS106 target polynucleotide sequence (which is referred to as the "amplification product(s)" or "amplicon(s)").

It will be understood that the exact amplification conditions required for step (b) in the method described above can be readily determined by one skilled in the art. Moreover, one skilled in the art will additionally understand that step (b) of the above method can be repeated several times by thermal cycling techniques in order to generate further copies of the BS106 target sequence.

The amplification product (or amplicon) produced by amplification of the BS106 target sequence as described above can be detected, either during or subsequent to said amplification, by a variety of methods known to one skilled in the art. Methods for detecting the amplification of a target sequence during amplification are described in U.S. Pat. No. 5,210,015 which is herein incorporated by reference. Additionally, the amplification product can be, but does not have to be, separated from the reaction components during detection.

In one aspect, the amplification product can be detected using gel electrophoresis, the techniques of which are known to one skilled in the art.

In another aspect, the amplification product can be detected using the probes of the present invention. For example, a probe that specifically hybridizes to a BS106 target sequence, has a length of 12 to 40 nucleotides and comprises a segment that is at least about 80% identical to the sequence set forth in SEQ ID NO: 4 can be included in the reaction mixture with the primers and subjected to the amplification conditions described above. Hence, such methods for detecting the amplified BS106 target sequence include the steps of (a) hybridizing at least one of the probes of the present invention to the BS106 target sequence, so as to form a hybrid comprising the probe and the BS106 target sequence; and (b) detecting the hybrid as an indication of the presence of the BS106 target sequence in the test sample.

Hybrids formed as above can be detected using microparticles and labels that can be used to separate and detect such hybrids. Detection can be performed according to the protocols used by the commercially available Abbott LCx® instrumentation (Abbott Laboratories; Abbott Park, Ill.).

In yet another aspect, the hybrids can be detected by incorporating labels in one or both of the primers and/or probes of the present invention to facilitate detection. Hence, first and second specific binding members attached to the primers and probe can be employed to immobilize the hybrids to microparticles and detect the presence of the microparticles with the assistance of a conjugate.

Alternatively, a combination of specific binding members and directly detectable labels can be employed to detect hybrids. For example, specific binding members can be introduced in the hybrids using primers labeled with specific binding members. A directly detectable label can be incorporated into the hybrids using a probe that has been labeled with a directly detectable label. Hence, hybrids can be immobilized to a microparticle using the specific binding member and directly detected by virtue of the label on the probe. It will be understood that other detection configurations are a matter of choice for those skilled in the art.

The primer sequence is employed to prime extension of a copy of a BS106 target sequence and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

In a preferred aspect, the amplification product produced by the amplification method described above is detected subsequent to the amplification of the BS106 target sequence by at least one probe sequence of the present invention. Preferably, the amplification product is not separated from the other reaction components. In fact, it is also preferred that the probe be included in the reaction mixture comprising the nucleic acid amplification reagents, the primers and the test sample. Hence, methods for detecting the amplified BS106 target sequence include the steps of (a) hybridizing at least one probe of the present invention to the BS106 target sequence, so as to form a hybrid comprising the probe and the BS106 target sequence; and (b) detecting the hybrid as an indication of the presence of the target sequence in the test sample. This hybrid can be detected by using routine techniques known in the art. Preferably, the probe has the sequence shown in SEQ ID NO: 5 and has been labeled with at least one fluorophore and at least one quencher.

If the probe is initially included as part of the reaction mixture, the primers, probe and amplification conditions selected are such that the probe sequence has a lower melt temperature than the primer sequences so that upon placing the reaction mixture under amplification conditions copies of the target sequence is produced at temperature above the $T_m$ of the probe. After such copies are synthesized, they are denatured and the mixture is cooled to enable the formation of hybrids between the probes and any copies of the BS106 target sequence. The rate of temperature reduction from the denaturation temperature down to a temperature at which the probes will bind to single stranded copies is preferably quite rapid (for example less than one minute to 5 minutes) and particularly through the temperature range in which an enzyme having polymerase activity is active for primer extension. Such a rapid cooling favors copy sequence/probe hybridization rather than primer/copy sequence hybridization and extension.

The primer pair and probe set of the present invention can be used in a real-time RT-PCR assay. A real-time RT-PCR assay has the advantage of being able to quantitate and set positivity cut-offs to differentiate populations of low gene expression from the population of interest. A real-time RT-PCR assay is better than gel detection of BS106 RNA. The primer pair and probe set of the present invention is also better than other primer pair and probe sets known in the art which usually create much longer amplicon sequences than those of the present invention. It is known that assay sensitivity becomes impaired when amplicon sequences are longer than 150 bp due to the RNA degradation that occurs in the cells during sample processing, particularly in RNA prepared from formalin fixed tissue. When the primers and probe of the present invention are combined with an RT-PCR amplification master mix containing a hot start enzyme and real-time RT-PCR detection, they yield an assay with specific detection of BS106 and a sensitivity of 2 copies of RNA.

Kits

The primers and probes of the present invention can be provided as part of a kit that allows for the detection of a BS106 target sequence in a test sample. Such kits can be used to detect or identify breast cancer in a mammal, which is preferably a human. In one embodiment, the kit comprises at least two primers and at least one probe. Preferably, one of the primers has a length of 15 to 40 nucleotides and comprises a segment that is at least about 80% identical to SEQ ID NO: 2 and the second primer has a length of 15 to 40 nucleotides and comprises a segment that is at least 80% identical to SEQ ID NO: 3 and the probe has a sequence has a length of 12 to 40 nucleotides and comprises a segment that is at least about 80% identical to the sequence set forth in SEQ ID NO: 4. In another embodiment, the kit comprises primers having the sequence shown in SEQ ID NOS: 2 and 3 and a probe having the sequence shown in SEQ ID NO: 5.

The kits can optionally include amplification reagents, reaction components, and/or reaction vessels. One or more of the primers and/or probes can incorporate a detectable label or one or more fluorophores and quenchers, or the kit may include reagents for labeling the polynucleotides. One or more of the components of the kits may be lyophilized and the kit may comprise reagents suitable for the reconstitution of the lyophilized components. The kit can additionally contain instructions for use.

Applications

The primers and probes of the present invention can find application in clinical or research settings for identifying mammals, preferably humans, which either have or are at risk of developing breast cancer. The identification of breast cells outside the breast, such as in the peripheral blood, lymph nodes or bone marrow, for example, could indicate that breast cancer cells are metastasizing. Physicians could use this information to modify the assigned stage of a patient's breast cancer, thus leading to potentially more appropriate treatments. Alternatively, physicians could monitor peripheral blood to assess the efficacy of current treatment, allowing an earlier switch to a more effective treatment if circulating breast cells are detected. In a further potential application, physicians could periodically test breast cancer patients after completion of treatment to monitor for the return of disease.

The following examples are provided to further illustrate the present invention and are not intended to limit the invention.

EXAMPLES

The following examples demonstrate detection of BS106 using the DNA oligomer primers and probes provided herein. These DNA primers and probes are identified as SEQ ID NO: 2, SEQ ID NO: 3 and SEQ ID NO: 5. A portion of the BS106 consensus sequence is designated as SEQ ID NO: 1. The nucleotide sequences useful in the context of the present invention are:

```
SEQ ID NO: 1: ACCATGAAGTTCTTAGCAGTCCTGGTACTCTTG
              GGAGTTTCCATCTTTCTGGTCTCTGCCCAGAATC
              CGACAACAGCTGCTCCAGCTGACACGTATCCAG
              CTACTGGTCCTGCTGATGAT

SEQ ID NO: 2: 5' ACC ATG AAG TTC TTA GCA GTC '3

SEQ ID NO: 3: 5' ATC ATC AGC AGG ACC AGT AGC '3

SEQ ID NO: 5: FAM-GTGCTG CCCAGA ATCCGAC AACAGCAC-
              Quencher
```

In the following examples, SEQ ID NO: 2 and SEQ ID NO: 3 are used as amplification primers specific for the BS106 cDNA consensus sequence (SEQ ID NO:13). SEQ ID NO: 5 is used as an internal hybridization probe for the BS106 amplification product.

Example 1

Preparation of BS106 Primers and Probes

A. BS106 Primers

Target-specific primers and probes were designed to amplify and detect the BS106 gene mRNA sequence by molecular beacon RT-PCR. These primers are shown in SEQ ID NO: 2, and SEQ ID NO: 3. Primer sequences were synthesized using conventional nucleotide phosphoramidite chemistry.

B. BS106 Probes

The detection probe was designed to hybridize with the amplified BS106 target sequence by hybridization. Upon hybridization, the molecular beacon stem separates, allowing the 5' linked fluorophore to fluoresce since it is no longer in close proximity to the 3' Quencher. The probe is shown in SEQ ID NO: 5. The probe sequence was synthesized using conventional nucleotide phosphoramidite chemistry and labeled with a 6-FAM Fluorophore, from Applied Biosystems in Foster City, Calif. on the 5' end and a quencher, BHQ1, from Biosource Technologies, Inc. in Nevada, Calif. on the 3' end.

Example 2

Preparation of BS106 mRNA

BS106 RNA was extracted from the MDA-MB-361 Metastatic Breast Adenocarcinoma cell line obtained from American Type Culture Collection, ATCC #HTB-27, Manassas, Va.

RNA was extracted and purified from the MDA-MB-361 cell cultures using the RNeasy® RNA Isolation kit from Qiagen, Valencia, Calif., following the manufacturer's directions. Purified RNA was quantitated by spectrophotometry using an absorbance reading at 260 nm and an extinction coefficient of 40, or quantitated on a per cell basis. Copy number per cell was determined by performing real-time RT-PCR, as described in EXAMPLE 3A on 40 replicates of two levels of RNA that are on the border of detection. Copy number was calculated using the Poisson distribution calculation of copy number=–natural log (number of replicates missed/total number of replicates).

Example 3

Detection of BS106

A. Amplification and Detection of BS106

Preparation of cDNA, PCR amplification and detection of BS106 were performed in a quantitative one-step real time RT-PCR reaction in which all of the reagents for preparation of cDNA, amplification and detection are combined at the start of the reaction and each reaction occurs sequentially within one sealed well. BS106 purified RNA (prepared as described in EXAMPLE 2) was serially diluted from 10,000 to 2 copies/5 µl in 20 ng/µl poly A (equivalent to 120 to 0.024 MDA-MB-361 cells/5 µl). Five µl of diluted BS106 RNA samples were added to wells in a chilled optical 96 well amplification plate purchased from Applied Biosystems, Foster City, Calif., prior to the addition of 45 µl master mix solution containing: 1× QUANTITECT™ probe RT-PCR master mix and 0.5 U QUANTITECT™ RT mix obtained from Qiagen, Valencia, Calif., 500 nM of SEQ ID NO: 2, 800 nM of SEQ ID NO: 3, and 150 nM of SEQ ID NO: 5. Testing was done in replicates of 3 for all of the samples except for the 2 copy level, which was performed in replicates of 6. 100 ng Poly A (Amersham Biosciences, Piscataway, N.J.) and 50 ng Raji cell line RNA (cells obtained from ATCC #CCL-86, Manassas, Va. and RNA purified as described in EXAMPLE 2) served as negative controls.

The 96 well amplification plate was then sealed with optical sealing film, centrifuged at 6,000 rpm for 1 minute in a Sigma-Qiagen 14-C plate centrifuge and then loaded into the ABI PRISM 7000™ instrument from Applied Biosystems. The reaction mixes were cycled in the ABI PRISM 7000™ at 50° C. for 30 minutes to prepare cDNA and 94° C. for 15 minutes to inactivate the RT enzymes and activate the DNA Polymerase. The reaction mixtures were immediately PCR amplified by cycling at 94° C. for 15 seconds/63° C. for 30 seconds for 5 cycles and 94° C. for 15 seconds/62° C. for 30 seconds/47° C. for 30 seconds for 40 cycles.

Reaction products were detected by the instrument taking fluorescent readings during each 47° C. cycling step and generating a real-time amplification plot to determine the cycle number that corresponded to the rise of FAM fluorophore (threshold cycle, $C_t$). The threshold cycles and standard deviations (SD) are presented in TABLE 1 and show specific detection of BS106 RNA from as little as 0.024 MDA-MB-361 cells (2 copies).

TABLE 1

| Sample | Concentration Per reaction | Threshold cycle ($C_t$) | Threshold cycle (SD) |
|---|---|---|---|
| 10,000 copies | 120 MDA-MB-361 cells | 20.62 | 0.089 |
| 1,000 copies | 12 MDA-MB-361 cells | 24.14 | 0.126 |
| 100 copies | 1.2 MDA-MB-361 cells | 27.29 | 0.092 |
| 10 copies | 0.12 MDA-MB-361 cells | 30.92 | 0.313 |
| 2 copies | 0.024 MDA-MB-361 cells | 32.54 | 0.398 |
| Poly A | 100 ng | Not detected | 0 |
| Raji | 50 ng | Not detected | 0 |

Additionally, after the thermal cycling step above, a small amount of sample was removed and was visualized on a 10% polyacrylamide gel stained with SYBR® Green. The gel showed the expected 123 base pair product.

B. Sensitivity of Detection of BS106 from RNA

The purified RNA from the MDA-MB-361 cell line (prepared as described in EXAMPLE 2) was serially diluted from 10,000 to 2 copies/5 µl in 20 ng/µl poly A (equivalent to 120 to 0.024 MDA-MB-361 cells/5 µl) to serve as the standard curve samples. The number of copies of BS106 per cell was determined previously by a Poisson distribution experiment as described in EXAMPLE 2. Aliquots of the 100 copy and 10 copy standard curve samples above were further diluted with Raji cell line RNA (described in EXAMPLE 3A) and RNase/DNAse-free water to create 10 copy, 5 copy, and 2 copy BS106 RNA "unknown" samples in the presence of 50 ng Raji (Burkitt's lymphoma) negative control RNA. Five µl of the samples were added to 45 µl of master mix solution as described in EXAMPLE 3A. The 10,000 to 10 copy standard curve samples (in 10-fold dilutions), negative control samples, 2 copy standard curve sample, 10 copy unknown sample, 5 copy unknown sample and 2 copy unknown sample were performed in replicates of 3, 3, 6, 5, 5 and 8, respectively. Real-time RT-PCR was performed as described above in EXAMPLE 3A.

The assay had a PCR efficiency of 103.7% and $R^2$ of 0.994, as determined by the standard curve values and calculated by the ABI PRISM 7000™ software version 1.1. The average $C_t$ and quantitation values from the this experiment and standard deviations (quantitated by the ABI PRISM 7000™ software) are presented in TABLE 2 and show detection of BS106 from as little as 2 copies of BS106 RNA in a background of 50 ng RNA. Thus, this method, with these primers and probes, is capable of detecting very low levels of BS106 RNA in the presence of non-specific RNA, which could be important in a clinical setting since circulating tumor cells occur at low levels and will always be in the presence of background cells.

TABLE 2

| Sample | Threshold cycle ($C_t$) | Threshold cycle (SD) | Quantitation (copies) | Quantitation (SD) |
|---|---|---|---|---|
| 10 copies BS106 RNA + 50 ng Raji RNA | 30.47 | 0.517 | 10.84 | 4.13 |
| 5 copies BS106 RNA + 50 ng Raji RNA | 31.06 | 0.793 | 7.55 | 3.67 |
| 2 copies BS106 RNA + 50 ng Raji RNA | 32.70 | 1.585 | 3 | 2.14 |
| 100 ng Poly A RNA | Not detected | 0 | 0 | 0 |
| 50 ng Raji RNA | Not detected | 0 | 0 | 0 |

Example 4

Comparison of Multiple Primer/Probe Sets

A comparison was made between the use of SEQ ID NO: 2, SEQ ID NO: 3, and SEQ ID NO: 5 and the sequence pairs listed in TABLE 3. BS106 specific PCR products were previously observed on a 4% agarose gel stained with SYBR® Green for 100 and 1 MDA-MB-361 cell samples/reaction for primer pairs 1, 2, and 3 but no PCR product was visualized for primer pair 4. Therefore, pairs 1 through 3 were further evaluated for sensitivity and specificity with the beacon probe in a real-time RT-PCR assay.

Purified MDA-MB-361 RNA, as described in EXAMPLE 2, was diluted in 10 fold serial dilutions from 50 to 0.5 cells/reaction in 20 ng poly A (Amersham Biosciences, Piscataway, N.J.). Five µl of diluted BS106 RNA samples were added to wells in a chilled optical 96 well amplification plate purchased from Applied Biosystems, Foster City, Calif., prior to the addition of 45 µl master mix solution containing: 1× PROMEGA ACCESS™ RT-PCR master mix, 2.5 mM MgSO$_4$, 200 µM dNTP, 0.1 U AMV RT enzyme and 0.1 U Tfl DNA polymerase, all obtained from Promega, Madison, Wis., and 200 nM each forward/reverse primer and 300 nM beacon probe from primer/probe pairs 1, 2, and 3 listed in TABLE 3. Testing was done in replicates of 2 with 100 ng poly A and 50 ng human genomic DNA (BD Biosciences/Clonetech, Palo Alto, Calif.) as the negative controls.

TABLE 3

| PAIR # | Forward Primer | Reverse Primer | Beacon/Probe |
|---|---|---|---|
| 1 | SEQ ID NO: 2 | SEQ ID NO: 3 | SEQ ID NO: 5 |
| 2 | SEQ ID NO: 6 | SEQ ID NO: 3 | SEQ ID NO: 7 |
| 3 | SEQ ID NO: 8 | SEQ ID NO: 9 | SEQ ID NO: 10 |
| 4 | SEQ ID NO: 11 | SEQ ID NO: 12 | SEQ ID NO: 10 |

```
SEQ ID NO: 2: 5' ACC ATG AAG TTC TTA GCA GTC '3
SEQ ID NO: 3: 5' ATC ATC AGC AGG ACC AGT AGC '3
SEQ ID NO: 5: FAM-GTGCTG CCCAGA ATCCGAC AACAGCAC-Quencher
SEQ ID NO: 6: 5' GCC CAG AAT CCG ACA ACA '3
SEQ ID NO: 7: FAM-CGCGTG TGCTCC AGCTGACACGTATC CACGCG-Quencher
SEQ ID NO: 8: 5' TCT ACC ACT GCT CGT AAA GAC '3
SEQ ID NO: 9: 5' CTC AGG GAC ACA CTC TAC CAT '3
SEQ ID NO: 10: FAM-GCGTG CAAATGGG TT GGGGATCT CACGC-Quencher
SEQ ID NO: 11: 5' TGC TTC TAC CAC TGC TCG TAA A 3'
SEQ ID NO: 12: 5' CCA TCT CAG GGA CAC ACT CTA CCA T '3
```

The 96 well amplification plate was then sealed with an optical sealing film, centrifuged at 6,000 rpm for 1 minute in a Sigma-Qiagen 14-C plate centrifuge and then loaded into the ABI PRISM 7000™ instrument from Applied Biosystems. The reaction mixes were cycled in the ABI PRISM 7000™ at 48° C. for 45 minutes to prepare cDNA and 95° C. for 1 minute to melt the cDNA. The reaction mixtures were immediately PCR amplified by cycling at 94° C. for 15 seconds/63° C. for 30 seconds for 5 cycles and 94° C. for 15 seconds/62° C. for 30 seconds/45° C. for 30 seconds for 40 cycles. The reaction products were detected as described in EXAMPLE 3A with the instrument taking fluorescent readings during each 45° C. cycling step.

The data from this experiment is shown in TABLE 4 and indicates that the use of primer/probe pairs 2 and 3 are not as useful to the assay since they result in false positives with either poly A or human placental DNA and therefore a loss in specificity.

TABLE 4

| Sample | Ct Pair 1 | Ct Pair 2 | Ct Pair 3 |
|---|---|---|---|
| 50 MDA-MB-361 cells | 22.95 | 21.68 | 21.47 |
| 5 MDA-MB-361 cells | 26.34 | 25.04 | 25.33 |
| 0.5 MDA-MB-361 cells | 29.99 | 28.4 | 28.6 |
| 100 ng Poly A | Not detected | 38.94 | 25.44 |
| 50 ng human genomic DNA | Not detected | 32.88 | Not detected |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms.

What is claimed is:

1. A composition of matter comprising
   (a) an isolated first primer consisting of SEQ ID NO:2, and
   (b) an isolated second primer consisting of SEQ ID NO:3.

2. A composition of matter for detecting a BS106 target sequence comprising
   (a) an isolated first primer consisting of SEQ ID NO:2,
   (b) an isolated second primer consisting of SEQ ID NO:3, and
   (c) an isolated probe consisting of 12 to 40 nucleotides, wherein the probe comprises SEQ ID NO:4, and wherein the probe comprises a detectable label capable of generating a measurable signal.

3. The composition of claim 2, wherein the probe segment consists of SEQ ID NO:5.

4. A kit for amplifying a BS106 target sequence comprising:
   (a) a first primer consisting of SEQ ID NO:2;
   (b) a second primer consisting of SEQ ID NO:3; and
   (c) amplification reagents.

5. The kit of claim 4, further comprising a probe consisting of 12 to 40 nucleotides, wherein the probe comprises SEQ ID NO:4, and wherein the probe comprises a detectable label capable of generating a measurable signal.

6. The kit of claim 4, further comprising a probe having a sequence consisting of SEQ ID NO:5, wherein the probe comprises a detectable label capable of generating a measurable signal.

* * * * *